US009179828B2

(12) United States Patent
Ono (10) Patent No.: US 9,179,828 B2
(45) Date of Patent: Nov. 10, 2015

(54) ELECTRONIC ENDOSCOPE APPARATUS (75) Inventor: Mitsunobu Ono, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 13 days.

(21) Appl. No.: 13/565,152

(22) Filed: Aug. 2, 2012

(65) Prior Publication Data

US 2013/0035545 A1    Feb. 7, 2013

Related U.S. Application Data (60) Provisional application No. 61/515,384, filed on Aug. 5, 2011.

(51) Int. Cl.
*A61B 1/00*     (2006.01)
*A61B 1/045*    (2006.01)
*A61B 1/05*     (2006.01)
*A61B 1/12*     (2006.01)
*H04N 5/376*    (2011.01)
*H04N 5/225*    (2006.01)

(52) U.S. Cl.
CPC . *A61B 1/045* (2013.01); *A61B 1/05* (2013.01); *A61B 1/128* (2013.01); *H04N 5/3765* (2013.01); *H04N 2005/2255* (2013.01)

(58) Field of Classification Search
CPC ...... A61B 1/00009; A61B 1/045; A61B 1/05; A61B 1/0638; A61B 1/128
USPC .......................................... 600/109, 117, 118
See application file for complete search history.

(56) References Cited

U.S. PATENT DOCUMENTS

| 2006/0287576 | A1* | 12/2006 | Tsuji et al. | 600/132 |
| 2008/0058602 | A1* | 3/2008 | Landry | 600/180 |
| 2008/0122942 | A1* | 5/2008 | Mimata et al. | 348/222.1 |
| 2008/0136903 | A1* | 6/2008 | Takada et al. | 348/65 |
| 2008/0158348 | A1* | 7/2008 | Karpen et al. | 348/82 |
| 2010/0240953 | A1* | 9/2010 | Murakami | 600/109 |
| 2012/0167882 | A1* | 7/2012 | Wood et al. | 128/204.17 |

FOREIGN PATENT DOCUMENTS

| JP | 06169888 A | 6/1994 |
| JP | 08024218 A | 1/1996 |
| JP | 2001-054027 A | 2/2001 |
| JP | 2005279253 A | 10/2005 |
| JP | 2005323884 A | 11/2005 |
| JP | 2007281759 A | 10/2007 |

* cited by examiner

*Primary Examiner* — Anhtuan T Nguyen
*Assistant Examiner* — Alexandra Newton
(74) *Attorney, Agent, or Firm* — Holtz, Holtz, Goodman & Chick PC (57) ABSTRACT

An electronic endoscope apparatus includes: a CCD; a temperature sensor that detects a temperature of a distal end portion; a correlated double sampling section provided in a body portion, the correlated double sampling section extracting a signal component from an image signal outputted from the CCD; a timing generator that generates a sample-and-hold signal for making the correlated double sampling section operate and a drive pulse signal for driving the CCD; and a CPU that adjusts a timing of the sample-and-hold signal or the drive pulse signal generated by the timing generator, based on the temperature detected by the temperature sensor.

18 Claims, 9 Drawing Sheets

TBL1

| NUMBER | TEMPERATURE OF DISTAL END PORTION (T1) | CORRECTION VALUE FOR SH1 | CORRECTION VALUE FOR SH2 | CORRECTION VALUE FOR ADCK |
|---|---|---|---|---|
| 1 | -10~19 | -1 | -1 | -1 |
| 2 | 20~39 | 0 | 0 | 0 |
| 3 | 40~59 | 0 | 0 | 0 |
| 4 | 60~79 | +1 | +1 | +1 |
| 5 | 80~99 | +2 | +2 | +2 |
| 6 | 100~110 | +3 | +3 | +3 |

FIG.4E CCD OUT

FIG.4H AFE IN

TBL2

| NUMBER | TEMPERATURE OF DISTAL END PORTION (T1) | CORRECTION VALUE FOR RG | CORRECTION VALUE FOR H1 | CORRECTION VALUE FOR H2 |
|---|---|---|---|---|
| 1 | −10~19 | −1 | −1 | −1 |
| 2 | 20~39 | 0 | 0 | 0 |
| 3 | 40~59 | 0 | 0 | 0 |
| 4 | 60~79 | +1 | +1 | +1 |
| 5 | 80~99 | +2 | +2 | +2 |
| 6 | 100~110 | +3 | +3 | +3 |

TBL3

| NUMBER | TEMPERATURE OF DISTAL END PORTION (T1) | TEMPERATURE OF BODY PORTION (T2) | CORRECTION VALUE FOR SH1 | CORRECTION VALUE FOR SH2 | CORRECTION VALUE FOR ADCK |
|---|---|---|---|---|---|
| 1 | −10~19 | −10~19 | 0 | 0 | 0 |
| 2 | −10~19 | 20~39 | −1 | −1 | −1 |
| 3 | −10~19 | 40~60 | −2 | −2 | −2 |
| 4 | 20~39 | −10~19 | 0 | 0 | 0 |
| 5 | 20~39 | 20~39 | 0 | 0 | 0 |
| 6 | 20~39 | 40~60 | −1 | −1 | −1 |
| 7 | 40~59 | −10~19 | 0 | 0 | 0 |
| 8 | 40~59 | 20~39 | 0 | 0 | 0 |
| 9 | 40~59 | 40~60 | 0 | 0 | 0 |
| 10 | 60~79 | −10~19 | +1 | +1 | +1 |
| 11 | 60~79 | 20~39 | +1 | +1 | +1 |
| 12 | 60~79 | 40~60 | 0 | 0 | 0 |
| 13 | 80~99 | −10~19 | +2 | +2 | +2 |
| 14 | 80~99 | 20~39 | +2 | +2 | +2 |
| 15 | 80~99 | 40~60 | +1 | +1 | +1 |
| 16 | 100~110 | −10~19 | +3 | +3 | +3 |
| 17 | 100~110 | 20~39 | +3 | +3 | +3 |
| 18 | 100~110 | 40~60 | +2 | +2 | +2 |

FIG.11

| NUMBER | TEMPERATURE OF DISTAL END PORTION | TEMPERATURE OF BODY PORTION | CORRECTION VALUE FOR RG | CORRECTION VALUE FOR H1 | CORRECTION VALUE FOR H2 |
|---|---|---|---|---|---|
| 1 | −10〜19 | −10〜19 | 0 | 0 | 0 |
| 2 | −10〜19 | 20〜39 | −1 | −1 | −1 |
| 3 | −10〜19 | 40〜60 | −2 | −2 | −2 |
| 4 | 20〜39 | −10〜19 | 0 | 0 | 0 |
| 5 | 20〜39 | 20〜39 | 0 | 0 | 0 |
| 6 | 20〜39 | 40〜60 | −1 | −1 | −1 |
| 7 | 40〜59 | −10〜19 | 0 | 0 | 0 |
| 8 | 40〜59 | 20〜39 | 0 | 0 | 0 |
| 9 | 40〜59 | 40〜60 | 0 | 0 | 0 |
| 10 | 60〜79 | −10〜19 | +1 | +1 | +1 |
| 11 | 60〜79 | 20〜39 | +1 | +1 | +1 |
| 12 | 60〜79 | 40〜60 | 0 | 0 | 0 |
| 13 | 80〜99 | −10〜19 | +2 | +2 | +2 |
| 14 | 80〜99 | 20〜39 | +2 | +2 | +2 |
| 15 | 80〜99 | 40〜60 | +1 | +1 | +1 |
| 16 | 100〜110 | −10〜19 | +3 | +3 | +3 |
| 17 | 100〜110 | 20〜39 | +3 | +3 | +3 |
| 18 | 100〜110 | 40〜60 | +2 | +2 | +2 |

ELECTRONIC ENDOSCOPE APPARATUS

This application claims priority under USC §119(e) of U.S. Provisional Patent Application Ser. No. 61/515,384 filed Aug. 5, 2011, which is incorporated herein by reference.

BACKGROUND OF THE INVENTION

1. Field of the Invention

The present invention relates to an electronic endoscope apparatus, and to an electronic endoscope apparatus that can properly perform correlated double sampling processing according to a temperature of a use environment of a distal end portion of an insertion portion.

2. Description of Related Art

Conventionally, endoscope apparatuses have widely been used for various types of inspections in the medical field and the industrial field. Endoscope apparatuses include an elongated insertion portion, a body portion, and a monitor provided in or connected to the body portion.

In the industrial field, endoscope apparatuses are sometimes used in various temperature environments such as inspections of buildings in outdoor sites with subzero temperatures, inspections of inner portions of jet engines, which have temperatures exceeding 100° C.

A user, which is an inspector, conducts an inspection by inserting an elongated insertion portion into an object to be inspected, and making an image of a site to be inspected, which is picked up by an image pickup device such as a CCD provided at a distal end of the insertion portion, be displayed on a monitor or stored in a storage device.

The image pickup device provided at the distal end of the insertion portion is driven by a drive circuit in the body portion, and an image signal outputted from the image pickup device is subjected to correlated double sampling processing for, e.g., denoising in a correlated double sampling circuit in an image signal processing section in the body portion.

Incidentally, the operation timings of electronic components including semiconductor devices change according to the temperature of the use environment. Thus, for example, Japanese Patent Application Laid-Open Publication No. 2001-54027 proposes a technique that delays the operation timing of a drive circuit for an image pickup device according to the temperature of the digital camera in order to properly process image signals from the image pickup device.

SUMMARY OF THE INVENTION

An aspect of the present invention provides an electronic endoscope apparatus including: an image pickup device provided in a distal end portion of an insertion portion of an endoscope; a first temperature detection section that detects a first temperature of the distal end portion; a correlated double sampling section provided in a body portion to which a proximal end of the insertion portion of the endoscope is connected, the correlated double sampling section extracting a signal component from an image signal outputted from the image pickup device; a cable that transmits an electric signal between the distal end portion and the body portion; a timing generating section provided in the body portion, the timing generating section generating a sample-and-hold signal for making the correlated double sampling section operate and a drive pulse signal for driving the image pickup device; and a timing adjusting section that adjusts a timing of the sample-and-hold signal or the drive pulse signal generated by the timing generating section, based on the first temperature detected by the first temperature detection section.

DETAILED DESCRIPTION OF PREFERRED EMBODIMENTS

Hereinafter, embodiments of the present invention will be described with reference to the drawings.

First Embodiment

Figure 1:
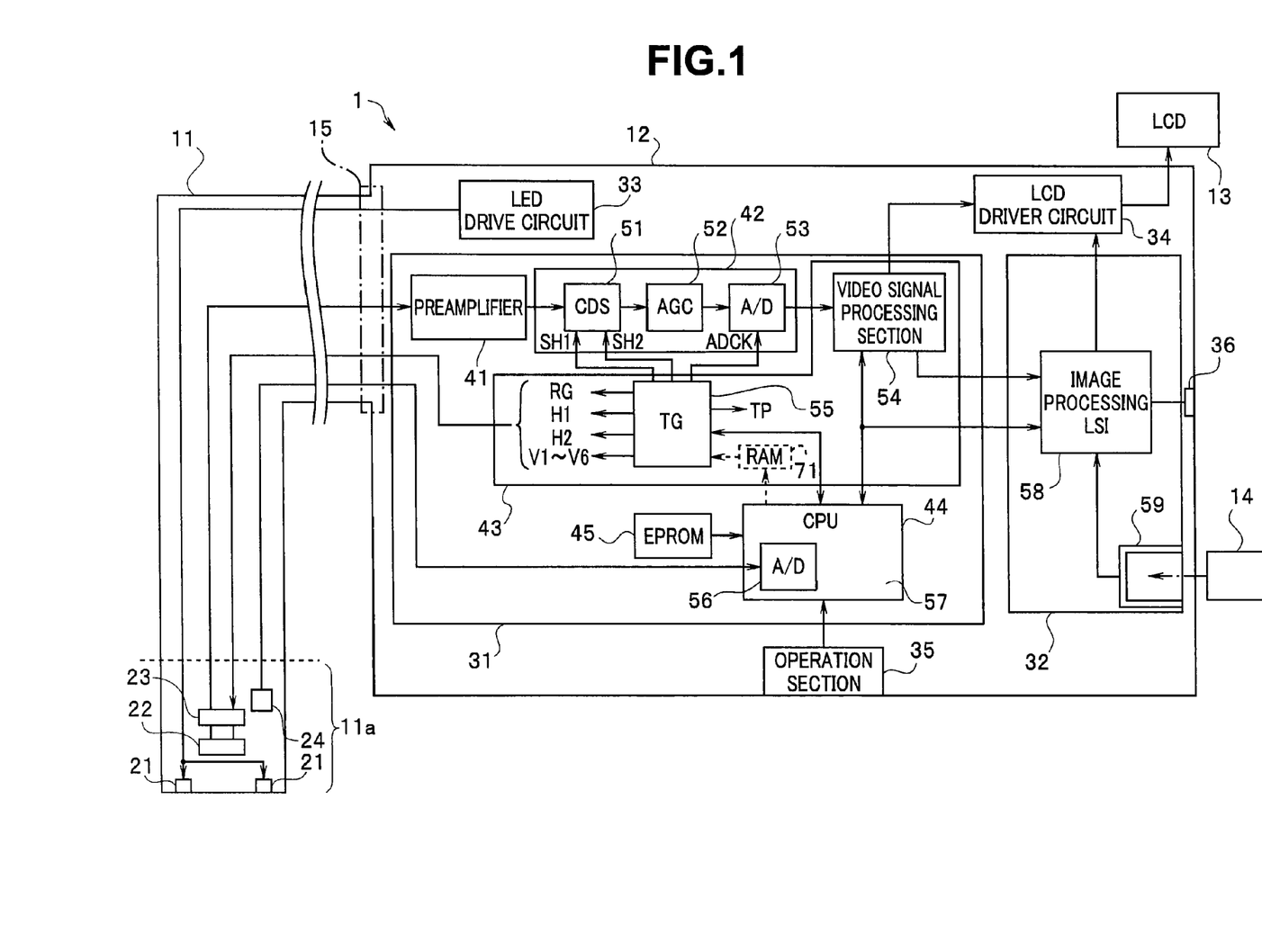
FIG. 1 is a configuration diagram illustrating a configuration of an endoscope apparatus according to a first embodiment of the present invention.

FIG. 1 is a configuration diagram illustrating a configuration of an endoscope apparatus according to the present embodiment. An endoscope apparatus 1 is an electronic endoscope apparatus including an elongated insertion portion 11, a body portion 12 to which a proximal end of the insertion portion 11 is connected, and a liquid-crystal display device (hereinafter referred to as LCD) 13, which is a display section connected to the body portion 12. A user, which is an inspector, can conduct an inspection by inserting a distal end portion of the insertion portion 11 into an apparatus to be inspected, and making an endoscopic image of a site to be inspected be displayed on the LCD 13. Also, the endoscopic image can be recorded on a recording medium 14, which is detachable from the body portion 12.

As indicated in the alternate long and short dash line in FIG. 1, the insertion portion 11 may be connected to via a connector 15 of the body portion 12 so that the insertion portion 11 is detachable from the body portion 12.

Furthermore, although the connection portion of the connector 15 can be separated from the insertion portion 11 at a position ahead of a preamplifier 41 and a timing generating circuit 55, which will be described later, in the present embodiment, alternatively, it is possible that the connection portion of the connector 15 is detachable from the insertion portion 11 at a digital signal part. For example, a configuration in which an analog front-end section 42 and a timing generating circuit 55 (a part of a field programmable gate array 43), which will be described later, are included in the insertion portion 11 side may be employed. Such configuration enables collection of all of factors of generation of timing lags on the insertion portion 11 side, and thus, where a detachable system is provided, adjustment for combination of the insertion portion 11 side and the body portion 12 side can be eliminated.

At a distal end portion 11a of the insertion portion 11, a plurality of (two in FIG. 1) light-emitting diodes (hereinafter referred to as LEDs) 21 are provided as an illumination section. The LEDs 21 are arranged around a non-illustrated observation window. Inside the observation window, a non-illustrated objective optical system is arranged, and at a focal position of the objective optical system, a CCD 22, which is an image pickup device, is arranged. In other words, the CCD 22 is an image pickup device provided at the distal end portion 11a of the insertion portion 11.

The CCD 22 is connected to the body portion 12 via a waveform shaping circuit 23. The waveform shaping circuit 23 includes a circuit that shapes waveforms of drive pulse signals (RG, H1 and H2) and supplies the drive pulse signals to the CCD 22, and a buffer circuit that performs impedance conversion of an image signal from the CCD 22.

Figure 2:
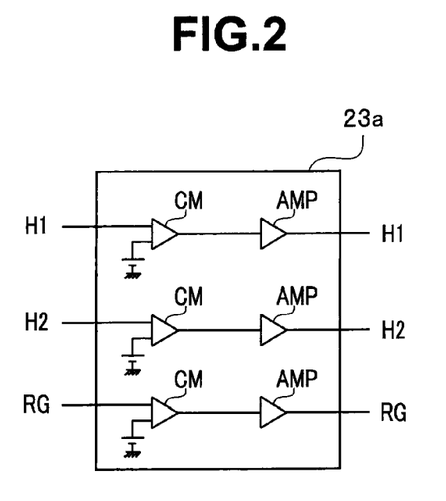
FIG. 2 is a circuit diagram of a circuit 23a that shapes waveforms of drive pulse signals (RG, H1 and H2) supplied to a CCD 22, according to the first embodiment of the present invention.

FIG. 2 is a circuit diagram of a circuit 23a that shapes the waveforms of the drive pulse signals (RG, H1 and H2) to be supplied to the CCD 22. The drive pulse signals (RG, H1 and H2) from the body portion 12 are inputted to respective amplifiers AMP via respective comparators CM that each compare the respective drive pulse signal with a predetermined threshold value, whereby respective drive pulses whose waveform have been shaped are supplied to the CCD 22.

Furthermore, in the distal end portion 11a of the insertion portion 11, a temperature sensor 24 for detecting a temperature of the distal end portion 11a is provided in the vicinity of the CCD 22. The temperature sensor 24, which is a temperature detection section, is, for example, a thermistor. From the viewpoint of easiness of attachment and fixing, the temperature sensor 24 is mounted on, for example, a circuit substrate on which the waveform shaping circuit 23 is mounted.

The body portion 12 includes a camera control unit (hereinafter referred to as CCU) 31, a recording and reproduction section 32, an LED drive circuit 33, an LCD driver circuit 34, an operation section 35 and an image signal output terminal 36.

The CCU 31 includes a preamplifier 41, an analog front-end section (hereinafter referred to as AFE) 42, a field programmable gate array (hereinafter referred to as FPGA) 43, a central processing unit (hereinafter referred to as CPU) 44, and an EPROM 45, which is a rewritable non-volatile memory.

The preamplifier 41 is a circuit that amplifies an image signal from the CCD 22, which is received via the buffer circuit in the waveform shaping circuit 23.

The AFE 42 includes a correlated double sampling circuit (hereinafter referred to as CDS section) 51, an automatic gain control circuit (hereinafter referred to as AGC section) 52 and an analog-digital conversion circuit (hereinafter referred to as A/D section) 53. The CDS section 51 receives an input of an image signal from the preamplifier 41, performs correlated double sampling processing on the image signal for denoising, based on sample-and-hold signals (SH1 and SH2), and outputs the image signal to the AGC section 52. In other words, the CDS section 51 is a correlated double sampling section provided in the body portion 12 to which the proximal end of the insertion portion 11 is connected, the correlated double sampling section extracting a signal component from an image signal outputted from the CCD 22.

The AGC section 52 adjusts a gain of the image signal from the CDS section 51, and outputs the image signal to the A/D section 53. The A/D section 53 converts the image signal, which is an analog signal, to a digital signal, and supplies the image signal to the FPGA 43.

The FPGA 43 includes a video signal processing section 54 and a timing generating circuit (hereinafter referred to as TG section) 55. The video signal processing section 54 processes the image signal from the AFE 42 based on a control signal from the CPU 44, and outputs the image signal to the LCD driver circuit 34 and the recording and reproduction section 32. The video signal processing section 54 supplies the live image signal from the CCD 22 to the LCD driver circuit 34. Also, the video signal processing section 54 converts the image signal from the CCD 22 to an image signal of a general-use format and outputs the image signal to the recording and reproduction section 32.

The TG section 55 generates and outputs various types of timing pulse signals under the control of the CPU 44. More specifically, the TG section 55 generates and outputs various types of drive signals (RG, H1, H2 and V1 to V6) for the CCD 22. Furthermore, the TG section 55 generates and outputs timing pulse signals (SH1, SH2 and ADCK) and outputs the timing pulse signals to the CDS section 51 and the A/D section 53. The CDS section 51 is driven by SH1 and SH2, which are two types of sample-and-hold pulse signals. Also, the TG section 55 generates and outputs various types of timing pulse signals TP in the FPGA 43. In other words, the TG section 55 provides a timing generating section provided in the body portion 12, the timing generating section generating a sample-and-hold signal for operating the CDS section 51 and a drive pulse signal for driving the CCD 22.

Also, while the TG section 55 generates a plurality of timing pulse signals such as described above, as described later, the TG section 55 is configured so as to adjust a timing of each timing pulse signal according to a correction instruction from the CPU 44.

The CPU 44 performs control of various types of circuits in the CCU 31 and the recording and reproduction section 32, based on instructions from an operation section 35 provided in the body portion 12, the operation section 35 including, e.g., switches operated by a user. Also, here, the CPU 44 includes an A/D section 56. The A/D section 56 converts an analog voltage signal from the temperature sensor 24 in the distal end portion 11a to a digital signal, and supplies the digital data on the temperature of the distal end portion 11a to the CPU 44. The CPU 44 calculates the temperature from the digital data from the temperature sensor 24.

The recording and reproduction section 32 includes an image processing LSI 58. The image processing LSI 58 is a circuit that encodes an image signal from the video signal processing section 54 based on a control signal from the CPU 44 and records the image signal onto the recording medium 14 via a connector 59, and also reads, decodes and reproduces an endoscopic image recorded in the recording medium 14 and outputs the endoscopic image to the LCD 13 via the LCD driver circuit 34. Also, the image processing LSI 58 can output an image signal via the image signal output terminal 36. The image processing LSI 58 includes scaling processing for image size conversion, and can output various types of image signals such as those of an analog VGA format, an SDI format or a VBS (composite video), S-video signals, or those of a DVI format via the image signal output terminal 36.

Instead of the aforementioned temperature sensor 24, a temperature detection section that detects a temperature of the distal end portion 11a from a DC component in an impedance conversion element, such as disclosed in Japanese Patent Application Laid-Open Publication No. 2007-125111 may be used.

The EPROM 45 is a memory that stores a correction value table storing correction value data, which will be described later. In the correction value table, phase adjustment times or pulse width adjustment information for various types of pulses, which are generated by the TG section 55, according to temperature data from the temperature sensor 24 are stored. The CPU 44 refers to the correction value table in the EPROM 45, reads a phase adjustment value or a pulse width adjustment value from the EPROM 45 based on the temperature data from the temperature sensor 24, and outputs the phase adjustment value or the pulse width adjustment value to the TG section 55 as correction value data. In other words, the CPU 44 and the TG section 55 provide a timing adjusting section that refers to a table storing a correction value for timing correction, and adjusts a timing of the sample-and-hold signal or the drive pulse signal using a correction value read from the table, the correction value corresponding to the temperature.

Also, the CPU 44 can send temperature data from the temperature sensor 24 to the video signal processing section 54 in the FPGA 43 and the post-stage image processing LSI 58 by means of communications in order to display the temperature data on a screen of the LCD 13 as temperature information, and reduce, e.g., a brightness, a color tone and/or random noise of displayed video according to the temperature data. Accordingly, the CPU 44 and the LCD 13 provide a temperature display section that displays a temperature of the distal end portion 11a.

Figure 3:
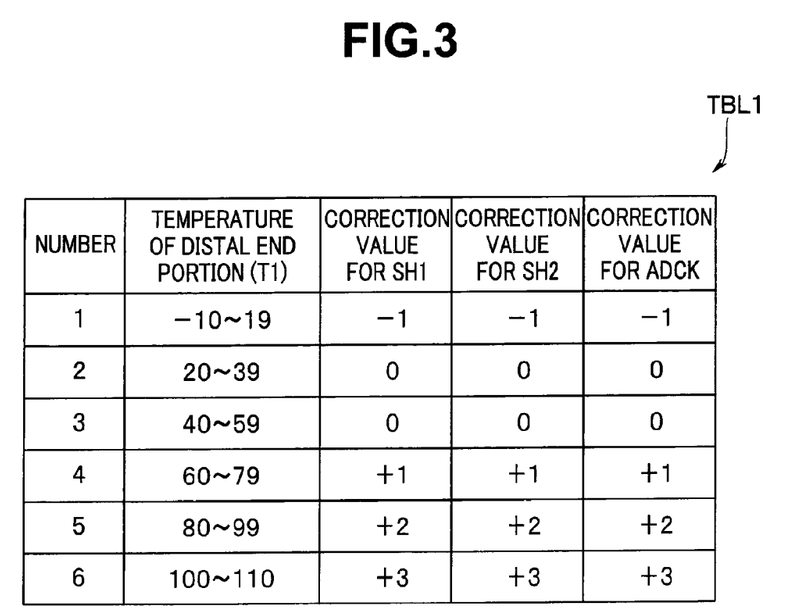
FIG. 3 is a diagram illustrating an example of a table of correction values for CDS timings, which is stored in an EPROM 45, according to the first embodiment of the present invention.

FIG. 3 is a diagram illustrating an example of a table of correction values for CDS timings, which is stored in the EPROM 45. A correction value table TBL1 stores respective correction values for the timing pulse signals SH1, SH2 and ADCK, which are provided to the CDS section 51 and the A/D section 53, according to temperatures T1 of the distal end portion 11a.

Figure 4A:
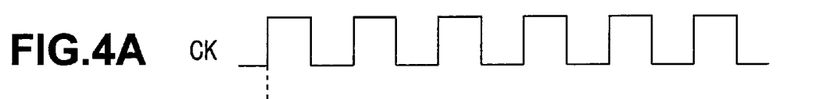
FIGS. 4A to 4J are timing charts of drive pulse signals inputted to the CCD 22, image signals and sample-and-hold signals relative to a clock signal CK, according to the first embodiment of the present invention.

FIGS. 4A to 4J are timing charts of drive pulse signals inputted to the CCD 22, image signals and sample-and-hold signals, relative to a clock signal CK. More specifically, FIGS. 4A to 4J are diagrams indicating drive pulse signals (RG, H1 and H2) inputted to the CCD 22 (FIGS. 4B, 4C and 4D), an output of the CCD 22 (CCD-OUT) (FIG. 4E) and ideal sample-and-hold signals (SH1_0 and SH2_0) (FIGS. 4F and 4G), and an image signal actually inputted to the AFE section 42 (AFE-IN) (FIG. 4H) and proper sample-and-hold signals (SH1 and SH2) (FIGS. 4I and 4J) relative to the clock signal CK (FIG. 4A).

The drive pulse signals supplied to the CCD 22 include three types of signals, i.e., a reset gate pulse signal (hereinafter referred to as RG signal) and horizontal transfer pulses H1 and H2, which are generated from the basic clock CK.

Figure 4B:
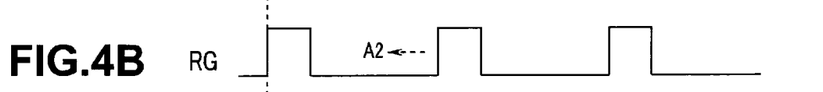
Figure 4C:
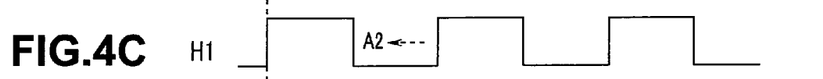
Figure 4D:
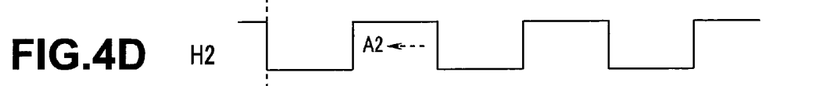

In FIGS. 4B, 4C and 4D, waveforms of the drive pulse signals (RG, H1 and H2) inputted to the CCD 22 are output waveforms immediately after the output of the waveforms from the waveform shaping circuit 23.

Figures 4E, 4F:
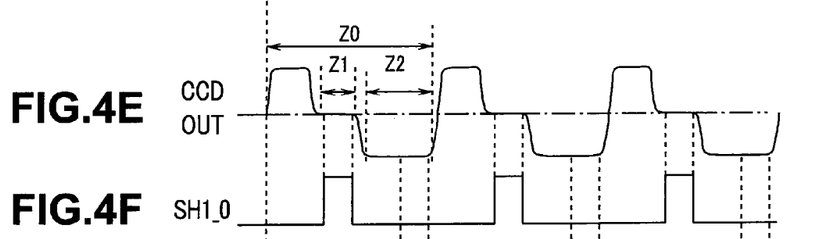
Figure 4G:
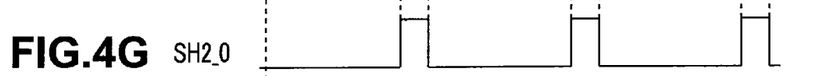

As a result of supply of the three types of drive pulse signals (RG, H1 and H2) to the CCD 22, a waveform like the output (CCD-OUT) is outputted from the CCD 22. The output (CCD-OUT) has an ideal waveform with very small distortion and/or delay. In FIGS. 4E to 4G, the ideal sample-and-hold signals (SH1_0 and SH2_0) are outputted at proper timings in a feed through period Z1 and a signal charge period Z2 for the output (CCD-OUT) of the image signal at an output terminal of the CCD 22. Also, the waveform of the output (CCD-OUT) corresponds to a pulse waveform of the RG signal, and the signal charge period Z2 in which the CCD 22 responds to light is determined by the timings of these three pulse signals (RG, H1 and H2).

In the case of an endoscope apparatus, drive pulse signals (RG, H1 and H2) generated by the TG section 55 in the body portion 12 are sent to the CCD 22 of the distal end portion 11a, and an image signal from the CCD 22 is outputted and returns to the body portion 12. The distal end portion 11a and the body portion 12 are connected via a cable for transmitting an electrical signal.

Figures 4H, 4I:
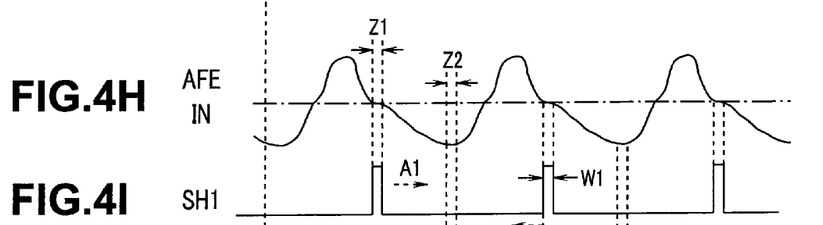
Figure 4J:
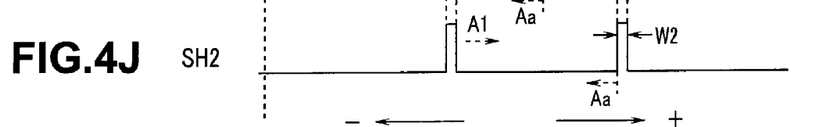

The waveform (FIG. 4H) of the image signal (AFE-IN) inputted to the AFE 42 via the cable, which is a thin signal wire, in the elongated insertion portion 11 becomes dull, and thus, the feed through period Z1 and the signal charge period Z2 are both shortened (FIGS. 4I and 4J). Furthermore, because of propagation in the thin and long signal wire, an electrical delay of no less than several tens of nanoseconds occurs between the output (CCD-OUT) and the image signal (AFE-IN), and in addition, the propagation delay time of the image signal from the CCD 22 changes depending on the temperature around the CCD 22, and variations of around several nanoseconds occurs in the time of the image signal returning to the CDS section 51.

For example, where the CCD 22 has 250,000 pixels, a one-pixel period Z0 is approximately 100 nsec (nanoseconds), and a stable period of each of the feed through period Z1 and the signal charge period Z2, during which sampling and holding are performed in the CDS section 51, is around 5 to 10 nsec, and thus, no large problem occurs even though a time lag of several nanoseconds (that is, phase shifting) occurs. However, in the case of, for example, 1,000,000 pixels, the one-pixel period Z0 is only approximately 25 nsec, and only a period of 2 to 4 nsec can be provided for a stable period of each of the feed through period Z1 and the signal charge period Z2, during which sampling and holding are performed in the CDS section 51.

Accordingly, a delay of several nanoseconds in image signal from the CCD 22 results in a failure of proper sample-and-hold processing in the CDS section 51, and thus, a normal video signal cannot be obtained in the CDS section 51, and at worst, an endoscopic image cannot be displayed. In the case of the endoscope apparatus 1, as illustrated in FIGS. 4I and 4J, the timings of the sample-and-hold signals (SH1 and SH2) are different from the aforementioned timings of the ideal sample-and-hold signals (SH1_0 and SH2_0) for the output (CCD-OUT) immediately after the output from the CCD 22 because of the temperature of the distal end portion 11a.

Therefore, in the present embodiment, timings or pulse widths of the sample-and-hold signals (SH1 and SH2) are corrected according to the temperature of the distal end portion 11a.

The correction value table TBL1 in FIG. 3 includes correction values for timings (that is, phases) of the sample-and-hold signals (SH1 and SH2), and the conversion timing signal ADCK, which is provided to the A/D section 53. Here, temperatures T1 of the distal end portion 11a are classified into six ranges, i.e., −10° C. to 19° C., 20° C. to 39° C., 40° C. to 59° C., 60° C. to 79° C., 80° C. to 99° C. and 100° C. to 110° C. Accordingly, here, six patterns of correction value data are stored in the correction value table TBL1. For example, different correction values for the timing pulse signals SH1, SH2 and ADCK are provided depending on variations of the temperature T1 of the distal end portion 11a. The respective correction values are correction values for making the respective timing pulse signals (SH1, SH2 and ADCK) be outputted at proper timings in, e.g., the feed through period Z1 according to the temperature T1 of the distal end portion 11a.

In FIG. 3, as the temperature T1 of the distal end portion 11a increases, the waveform of the image signal inputted to the AFE section 42 become delayed, and thus, the correction values become larger. As illustrated in FIGS. 4A to 4J, as the temperature T1 of the distal end portion 11a increases, the feed through period Z1 and the signal charge period Z2 for the image signal become delayed, and thus, the timings of the sample-and-hold signals (SH1 and SH2) are shifted in a direction A1 indicated by a dotted line. In FIGS. 4A to 4J, the conversion timing signal ADCK, which is provided to the A/D section 53, is not indicated. In FIGS. 4A to 4J, the direction indicated by + is a direction in which the waveform of the image signal become delayed, and the direction indicated by − is a direction in which the waveform becomes advanced.

Accordingly, the CPU 44 adjusts the timings of the sample-and-hold signals (SH1 and SH2) and the conversion timing signal ADCK, which is provided to the A/D section 53, based on the temperature T1 of the distal end portion 11a.

Figure 5:
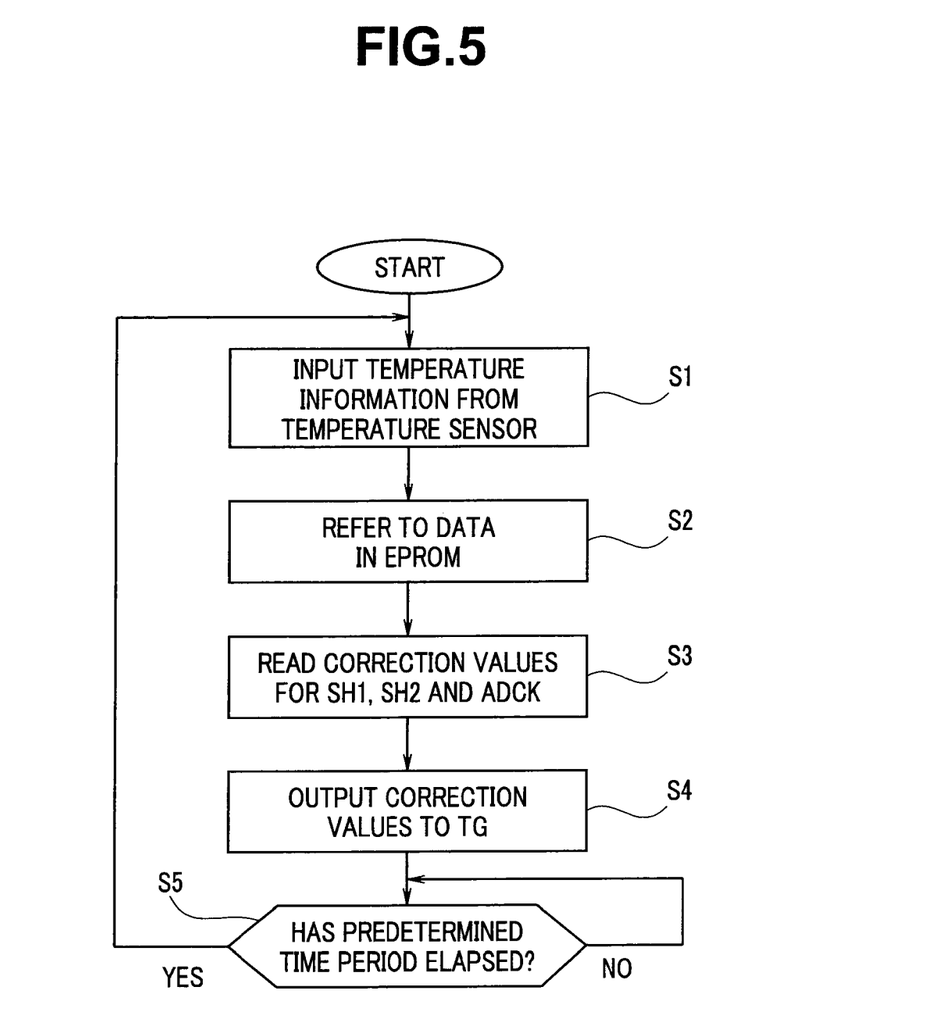
FIG. 5 is a flowchart illustrating an example of the flow of timing signal correction processing performed by a CPU 44, according to the first embodiment of the present invention.

FIG. 5 is a flowchart illustrating an example of the flow of timing signal correction processing performed by the CPU 44. The temperature T1 of the distal end portion 11a, that is, temperature information from the temperature sensor 24 is inputted to the CPU 44 (S1). Then, the CPU 44 refers to data in the correction value table TBL1 in the EPROM 45 (S2), and reads respective correction values for the sample-and-hold signals (SH1 and SH2) and the conversion timing signal ADCK, which is provided to the A/D section 53, according to the input temperature information (S3).

Then, the CPU 44 outputs the respective read correction values to the TG section 55 (S4). The TG section 55 outputs the respective timing signals (SH1, SH2 and ADCK) corrected based on the respective input correction values. More specifically, the CPU 44 adjusts the timings of the respective timing signals (SH1, SH2 and ADCK) by changing the phases of the respective timing signals (SH1, SH2 and ADCK). As a result, even if the temperature T1 of the distal end portion 11a changes, various types of timing signals are supplied to the CDS section 51 and the A/D section 53 at proper timings according to the temperature T1.

The CPU 44 determines whether or not a predetermined time period, for example, five seconds, has elapsed (S5), and if the predetermined time period has not elapsed (S5: NO), no processing is performed, and if the predetermined time period has elapsed (S5; YES), the processing returns to S1, and the above-described processing is repeated.

Accordingly, the respective timing signals (SH1, SH2 and ADCK) are supplied to the CCD 22 at proper timings according to the temperature T1, and thus, the correlated double sampling processing and the A/D conversion processing are properly performed.

Although FIG. 3 indicates correction values for correcting timings of the respective timing signals (SH1, SH2 and ADCK), an effect similar to that in the above case can be provided using correction values for correcting the pulse widths of the respective timing signals (SH1, SH2 and ADCK). In other words, the CPU 44 and the TG section 55, which provides the timing adjusting section, adjusts the timings of the respective timing signals (SH1, SH2 and ADCK) by changing the pulse widths of the sample-and-hold signals (SH1 and SH2) and the conversion timing signal ADCK, which is provided to the A/D section 53.

For example, in FIGS. 4A to 4J, pulse widths W1 and W2 of the sample-and-hold signals (SH1 and SH2) are changed by advancing timings of rising edges of the pulse widths W1 and W2 in the direction indicated by dotted arrow Aa to widen the pulse widths.

Also, it is possible that both the timings (that is, phases) and the pulse widths of the respective timing signals (SH1, SH2 and ADCK) are corrected simultaneously so that the respective timing signals (SH1, SH2 and ADCK) are supplied at proper timings. Even though both the timings and the pulse widths of the respective timing signals (SH1, SH2 and ADCK) are corrected, the respective timing signals (SH1, SH2 and ADCK) are supplied to the CCD 22 at proper timings according to the temperature T1, and thus, the correlated double sampling processing and the A/D conversion processing are properly performed.

Although the above-described example is an example in which the timings or the pulse widths of the sample-and-hold signals (SH1 and SH2) and the conversion timing signal ADCK, which is provided to the A/D section 53, are corrected, the timings (that is, phases) of drive pulse signals (RG, H1 and H2) may be corrected.

Figure 6:
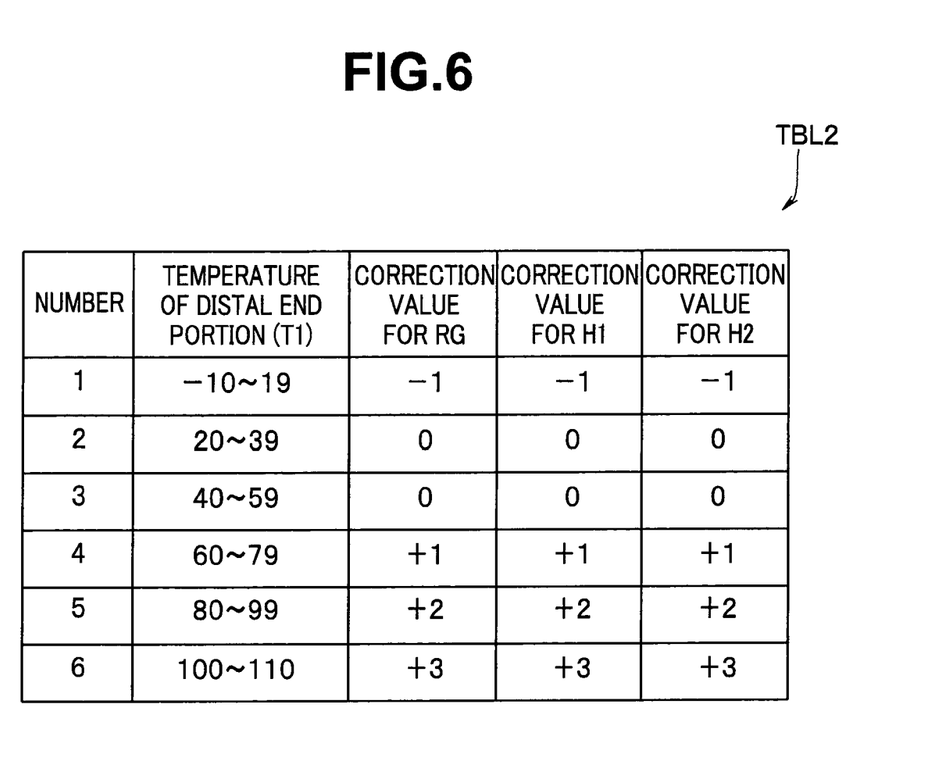
FIG. 6 is a diagram illustrating an example of a table of correction values for timings of drive pulse signals (RG, H1 and H2), which is stored in the EPROM 45, according to the first embodiment of the present invention.

FIG. 6 is an example of a table of correction values for timings of the drive pulse signals (RG, H1 and H2), which is stored in the EPROM 45. A correction value table TBL2 stores respective correction values for the drive pulse signals (RG, H1 and H2) supplied to the CCD 22.

In FIG. 6, as the temperature T1 of the distal end portion 11a increases, the waveform of the image signal inputted to the AFE section 42 becomes delayed, and thus, the respective correction values become larger. As illustrated in FIGS. 4A to 4J, as the temperature T1 of the distal end portion 11a increases, the feed through period Z1 and the signal charge period Z2 for the image signal become delayed, and thus, the timings of the drive pulse signals (RG, H1 and H2) are shifted in the direction A2 indicated by a dotted line.

The CPU 44 can make the timings of the sample-and-hold signals (SH1 and SH2) agree with the feed through period Z1 and the signal charge period Z2 using the correction value table TBL2 illustrated in FIG. 6, by outputting the correction values for the drive pulse signals (RG, H1 and H2) to the TG section 55, and thus, correlated double sampling processing is properly performed in the CDS section 51. The processing performed by the CPU 44 in this case is similar to the processing in FIG. 5, and is different from the processing in FIG. 5 only in that the referred table is the correction value table TBL2 for the timings of the drive pulse signals (RG, H1 and H2) and what is outputted by the CPU 44 are correction values for timings of the drive pulse signals (RG, H1 and H2).

Furthermore, together with the timings (that is, phases) or the pulse widths (or both of the phases and the pulse widths) of the sample-and-hold signals (SH1 and SH2), the timings (that is, phases) of the drive pulse signals (RG, H1 and H2) may be adjusted. In other words, the timings of both sample-and-hold signals (SH1 and SH2) and the drive pulse signals (RG, H1 and H2) may be adjusted so that correlated double sampling processing is properly performed.

As described above, in an electronic endoscope apparatus according to the above-described embodiment, even if a distal end portion of an elongated insertion portion of an endoscope in an electronic endoscope apparatus including the insertion portion is used in various temperature ranges, correlated double sampling processing is properly performed.

(Variation 1)

Although in the above-described endoscope apparatus 1, the CPU 44 refers to a correction value table in the EPROM 45 and supplies correction values to TG section 55 according to the temperature T1 of the distal end portion 11a, the TG section 55 may read correction values from a memory.

As indicated by a dotted line in FIG. 1, a configuration is made so that a RAM 71 is provided and a correction value table (TBL1 or TBL2) is transferred from the EPROM 45 to the RAM 71 and the TG section 55 refers to the correction value table and performs reading.

In this case, the CPU 44 notifies the TG section 55 of which correction value data in the correction value table is used according to the temperature of the distal end portion 11a, whereby the TG section 55 reads correction values and corrects and outputs timings or pulse widths of timing signals (drive pulse signals (RG, H1 and H2) and sample-and-hold signals (SH1 and SH2)).

Furthermore, although in the example in FIG. 1, the TG section 55 is included in the FPGA 43, alternatively, the TG section 55 may be included in the AFE section 42. This is because in recent years, a CCD drive frequency is increased along with an increase in number of pixels and in order to more stably perform correlated double sampling processing, there are more cases where the TG section 55 is included in the AFE section 42. Accordingly, the present embodiment can be applied to such cases.

Figure 7:
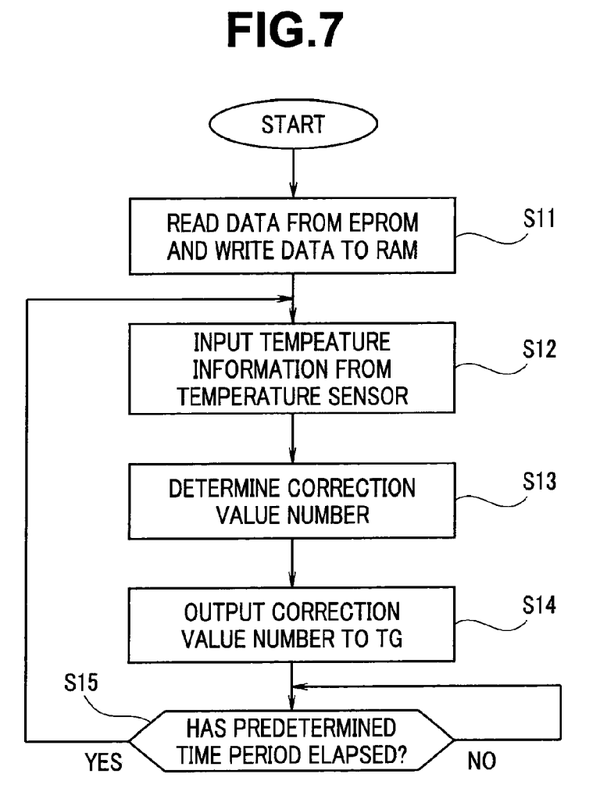
FIG. 7 is a flowchart illustrating an example of the flow of timing signal correction processing performed by the CPU 44, according to variation 1 of the first embodiment of the present invention.

FIG. 7 is a flowchart illustrating an example of a flow of timing signal correction processing performed by the CPU 44 according to the present variation. Here, although description will be provided taking the correction value table TBL1 as an example, and the same applies to a case of the correction value table TBL2.

The CPU 44 reads data in the correction value table TBL1 from the EPROM 45, and writes the data to the RAM 71 (S11). A temperature T1 of the distal end portion 11a, that is, temperature information from the temperature sensor 24 is inputted to the CPU 44 (S12). Then, the CPU 44 refers to data in the correction value table TBL1 in the EPROM 45 (S2) and determines a correction value number for respective correction values of the sample-and-hold signals (SH1 and SH2) and the conversion timing signal ADCK, which is provided to the A/D section 53, according to the input temperature information (S13). For example, in FIG. 3, if the temperature T1 of the distal end portion 11a is 45° C., the CPU 44 determines that the correction value number is "3".

Then, the CPU 44 outputs the determined correction value number to the TG section 55 (S14). The TG section 55 reads respective correction values corresponding to the input correction value number from the RAM 71, and outputs the respective timing signals (SH1, SH2 and ADCK) at corrected timings. As a result, even if the temperature T1 of the distal end portion 11a changes, various types of timing signals are supplied to the CDS section 51 and the A/D section 53 at proper timings according to the temperature T1.

The CPU 44 determines whether or not a predetermined time period, for example, five seconds, has elapsed (S15), and if the predetermined time period has not elapsed (S15: NO), no processing is performed, and if the predetermined time period has elapsed (S15: YES), the processing returns to S1 and the above-described processing is repeated.

Accordingly, in the present variation, also, the sample-and-hold signals (SH1 and SH2) are supplied at proper timings according to the temperature T1 of the distal end portion 11a, and thus, proper correlated double sampling processing is performed.

(Variation 2)

A variation of the waveform shaping circuit 23 will be described.

In the above-described endoscope apparatus 1, the CCD 22 in the distal end portion 11a is driven via signal wires inserted in the elongated insertion portion 11; however, the waveforms of drive pulse signals (RG, H1 and H2) inputted to the CCD 22 become dull due to RLC components in the signal wires when the drive pulse signals reach the distal end portion 11a, or are distorted due to, e.g., crosstalk between various types of signals. Such distortion, etc., become larger as the length of the insertion portion is larger. Thus, in particular, horizontal transfer pulses H1 and H2 are amended to each have a waveform with sharp edges using waveform shaping means to drive the CCD 22. This is because if edges of the waveform of the clocks of the horizontal transfer pulses H1 and H2 are not sharp, the horizontal transfer efficiency of the CCD 22 is decreased, causing deterioration in image quality.

As described above, in recent years, the one-pixel period Z0 is shortened because of an increase in number of pixels in an image pickup device. For example, while in the case of 250,000 pixels, the one-pixel period is approximately 100 nsec (nanoseconds), in the case of 1,000,000 pixels, the one-pixel period is approximately 25 nsec, which is approximately ¼ of that in the case of 250,000 pixels in principle. In this case, image quality deterioration may occur unless the pulse signal of the RG signal is also provided with shape edges, and thus, waveform shaping is required. Therefore, waveform shaping is required not only for H1 but also for RG.

Dullness or distortion of a waveform slightly changes depending on the specifications and/or the length of the signal wires and the status of the insertion portion, and thus, even if the waveform has been shaped by the waveform shaping circuit, then, a slight phase difference between the horizontal transfer pulses H1 and H2 occurs. When the horizontal transfer pulses H1 and H2 have phases opposite to each other, efficient horizontal transfer of charge in the image pickup device can be performed. However, if a slight phase difference between the horizontal transfer pulses H1 and H2 occurs due to some reason, the cross-switching characteristics of the horizontal transfer pulses H1 and H2 deteriorate, causing problems in image quality such as a failure of efficient charge transfer in the image pickup device. Therefore, it is important that the horizontal transfer pulses H1 and H2 have phases completely opposite to each other and the phase difference is prevented from occurring to the maximum possible extent.

Also, as the number of pixels in the image pickup device increases, the frequencies of the drive pulse signals (RG, H1 and H2) become higher, and thus, transmission loss and/or distortion of the long signal wires extending through the insertion portion 11 become larger. Thus, as an image pickup device with a larger number of pixels is used, it is necessary to provide thick signal wires, which then causes problems in design such as a failure of the signal wires to fall within a diameter of the insertion portion.

Therefore, attention is paid to the point that the horizontal transfer pulses H1 and H2 have phases opposite to each other, and in the present variation, only one of the horizontal transfer pulses H1 and H2 passing through the insertion portion 11 is transmitted, and the other horizontal transfer pulse H2 or H1 with a reversed phase is generated in the waveform shaping circuit.

Figure 8:
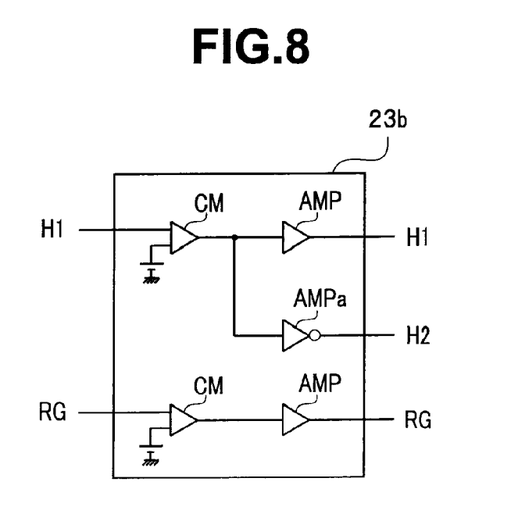
FIG. 8 is a circuit diagram of a circuit 23b that supplies drive pulse signals (RG, H1 and H2), according to variation 2 of the first embodiment of the present invention.

FIG. 8 is a circuit diagram of a circuit 23b that supplies drive pulse signals (RG, H1 and H2) according to the present variation. Respective drive pulses from the body portion 12 are of the RG signal and the horizontal transfer pulse H1, and the horizontal transfer pulse H2 is generated by inputting an output of a comparator CM that receives an input of the horizontal transfer pulse H1 and outputs a result of comparison of the horizontal transfer pulse H1 with a predetermined threshold value to an amplifier AMP that reverses a phase of the output and amplifies the output.

Therefore, according to the present variation, no phase difference occurs between the horizontal transfer pulses H1 and H2, and thus, the cross-switching characteristics of the horizontal transfer pulses H1 and H2 are improved, enabling an increase in charge transfer efficiency of the image pickup device.

Furthermore, although in the case of FIG. 2 or 8, waveform shaping is performed with one side of the comparator CM of the waveform shaping circuit 23 having a fixed DC potential, it is possible that the DC voltage is not fixed and the DC voltage is sent from the body portion 12 via a signal wire to perform waveform shaping. As the DC voltage changes, an operating point of the waveform shaping also changes, enabling a pulse width of an output waveform from the comparator CM to be changed. For example, it is possible that a digital output value from the CPU 57 is associated with the correction value table TBL2 to obtain an analog voltage value through a non-illustrated D/A converter, and the analog voltage that corresponds to the aforementioned DC voltage is sent as the DC voltage for the waveform shaping circuit 23. In other words, phase adjustment of the drive pulse signals (RG, H1 and H2) may be made by changing the operating point for the comparator CM in the waveform shaping circuit 23.

When timing adjustment of the sample-and-hold signals or the drive pulse signals is performed, noise may be superimposed on an output image from the AFL section 42 during the timing adjustment, depending on the type of the AFF section 42 that includes the CDS section 51. The image noise deteriorates the image quality. In order to avoid this, timing adjustment of the drive pulse signals is made in a period other than an image output period of the CCD 22, enabling effective removal of the noise. More specifically, timing adjustment of the sample-and-hold signals (SH1 and SH2) or the drive pulse signals (RG, H1 and H2) are made during a video image blanking period.

Also, making timing adjustment means that a sample-and-hold operation in the CDS section 51 slightly changes, and thus means that not only the image noise but also the brightness is slightly changed. If timing adjustment is frequently made, the brightness also frequently changes although the changes are slight ones, resulting in flickering in an image, which cause loss of stability of the image. In order to avoid this, the number selected for control may be prevented from frequently changing in the charts of the correction value tables TBL1 and TBL2. More specifically, for example, there is a division between 19° C. and 20° C., but, for example, a dead zone is provided for each division or a hysteresis characteristic is provided when the temperature changes across the division to perform control to prevent frequent change of the number selected for control.

Second Embodiment

While in the first embodiment, either or both of timings and pulse widths of various types of timing signals are corrected based on the temperature of the distal end portion 11a of the insertion portion 11, in the present embodiment, either or both of timings and pulse widths of various types of timing signals are corrected based not only on the temperature T1 of the distal end portion 11a but also on a temperature T2 of the body portion 12.

A temperature of the body portion 12 may largely change depending on the use environment of a user. For example, the temperature environment in which endoscope apparatuses are used are wide ranging from an frigid environment of 20° C. below zero to a scorching hot environment of 45° C. in which people can perform inspections.

Therefore, in the present embodiment, either or both of timings and pulse widths of various types of timing signals are corrected using a correction value table with both a temperature T1 of the distal end portion 11a and a temperature T2 of the body portion 12 taken into consideration.

Figure 9:
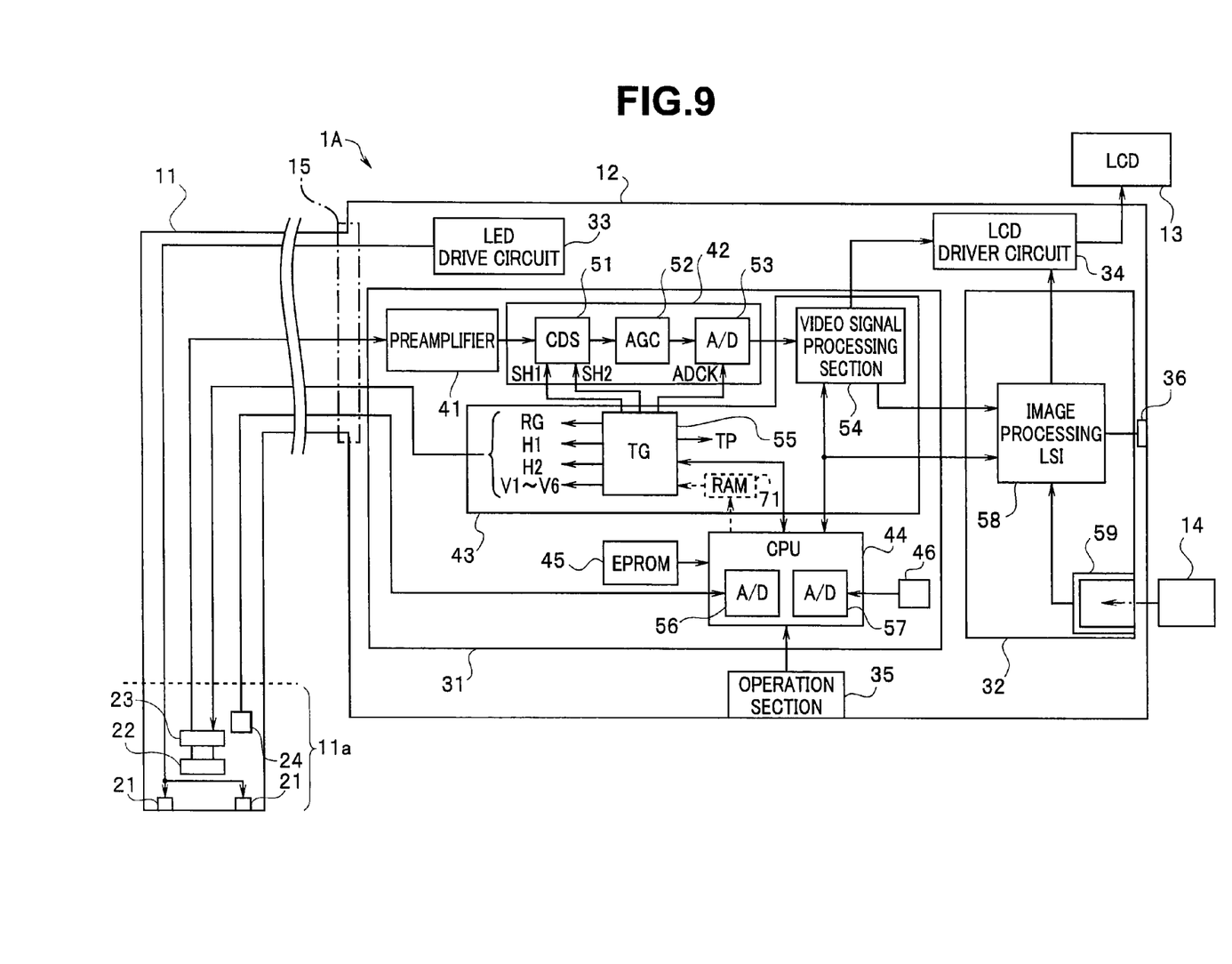
FIG. 9 is a configuration diagram illustrating a configuration of an endoscope apparatus according to a second embodiment of the present invention.

FIG. 9 is a configuration diagram illustrating a configuration of an endoscope apparatus according to the present embodiment. In FIG. 9, components that are the same as the components in FIG. 1 are provided with reference numerals that are the same as those in FIG. 1, and a description thereof will be omitted, and a description is provided on a configuration that is different from that of FIG. 1.

As illustrated in FIG. 9, in a CCU 31 in an endoscope apparatus 1A, a temperature sensor 46 for detecting a temperature of a body portion 12 is provided. Furthermore, a CPU 44 includes an A/D section 57. The A/D section 57 converts an analog signal from the temperature sensor 46 in the body portion 12 to a digital signal and supplies the data on the temperature of the body portion 12 to the CPU 44. The CPU 44 selectively receives a voltage signal from the temperature sensors 24 and 46, and calculates temperature information, respectively, from the digital data of the voltage signal.

The temperature sensor 46 is, for example, a thermistor. Various types of circuits in the CCU 31 include semiconductor devices, and thus, the temperature sensor 46 can detect the temperature of the body portion 12 by providing the temperature sensor 46 in the vicinity of the semiconductor devices.

Also, instead of the above-described temperature sensor 46, a temperature detection section that detects a temperature from a DC component in an impedance conversion element using a technique disclosed in Japanese Patent Application Laid-Open Publication No. 2007-125111 may be used.

An EPROM 45 stores a table including temperature information from the two temperature sensors 24 and 46, and phase adjustment times or pulse width adjustment information for various types of pulses generated by a TG section 55. The CPU 44 refers to data in the EPROM 45 and reads phase adjustment values or pulse width adjustment values from the EPROM 45 based on two pieces of temperature information with reference to the table, and outputs the phase adjustment values or the pulse width adjustment values to the TG section 55.

Also, the CPU 44 can send the temperature information to the video signal processing section 54 in the FPGA 43 and a post-stage image processing LSI 58 by means of communications in order to display the pieces of temperature information from the temperature sensors 24 and 46 on a screen of an LCD 13 as temperature information, and reduce, e.g., a brightness, a color tone and/or noise of, e.g., random noise of displayed video according to the temperature information.

Figure 10:
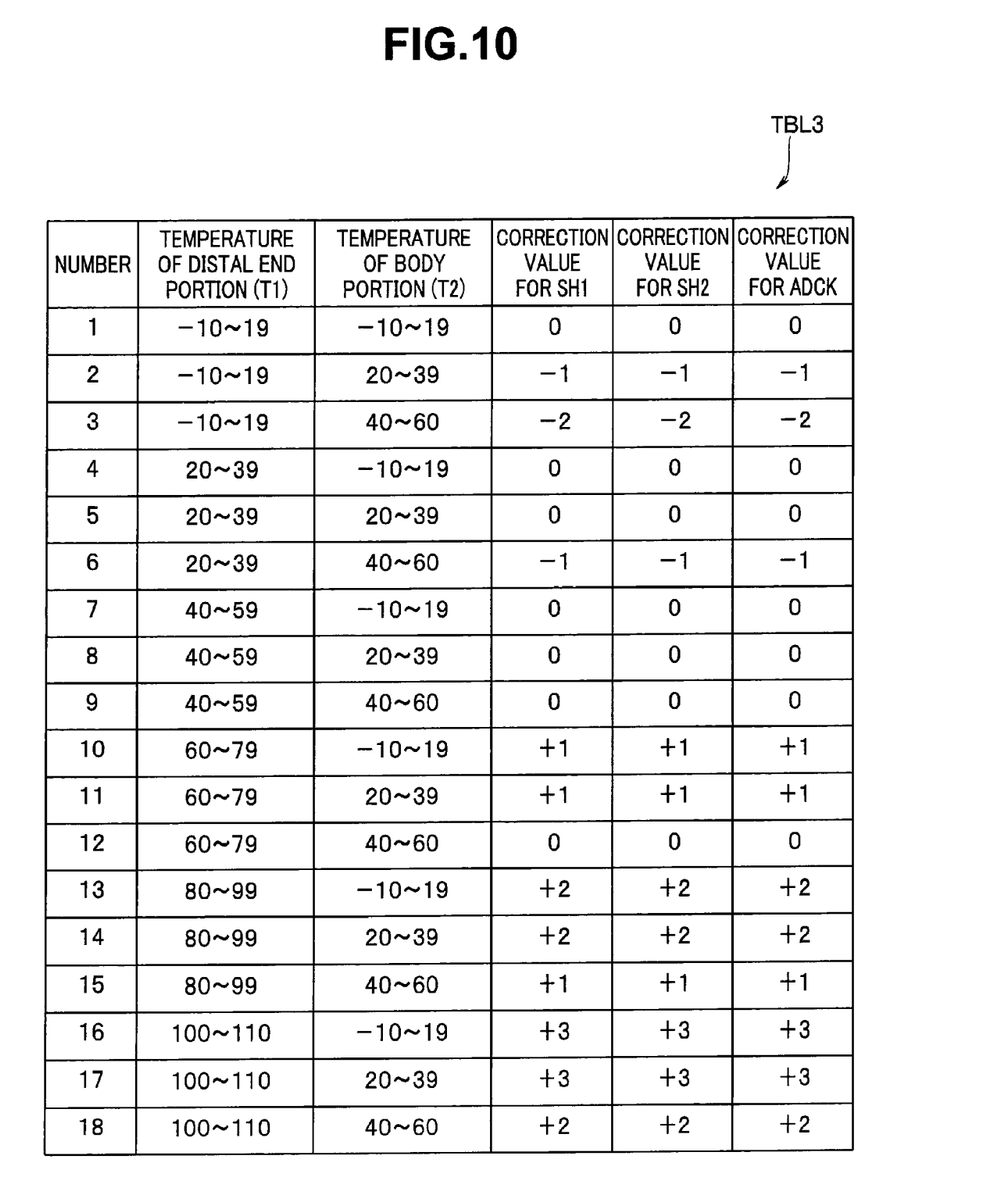
FIG. 10 is a diagram illustrating an example of a table of correction values for CDS timings, which is stored in an EPROM 45, according to the second embodiment of the present invention.

FIG. 10 is a diagram illustrating an example of a table of correction values for CDS timings, which is stored in the EPROM 45. A unit of the correction value is, for example, nsec (nanosecond). A correction value table TBL3 stores respective correction values for respective timing signals (SH1, SH2 and ADCK), which are provided to a CDS section 51 and an A/D section 53, according to combinations of temperatures T1 of the distal end portion 11a and temperatures T2 of the body portion 12.

Here, the temperatures T1 of the distal end portion 11a are classified into six ranges, i.e., −10° C. to 19° C., 20° C. to 39° C., 40° C. to 59° C., 60° C. to 79° C., 80° C. to 99° C. and 100° C. to 110° C., and the temperatures T2 of the body portion 12 are classified into three ranges, i.e., −10° C. to 19° C., 20° C. to 39° C. and 40° C. to 60° C. Then, the number of combinations of these classification ranges, here, 18 patterns of correction value data are stored in the correction value table TBL3. The respective correction values are correction values for making the respective timing signals (SH1, SH2 and ADCK) be outputted at proper timings in, e.g., a feed through period T1 according to the temperature T1 of the distal end portion 11a and the temperature T2 of the body portion 12.

For example, as the temperature T2 of the body portion 12 become higher relative to the temperature T1 of the distal end portion 11a, a waveform of an image signal inputted to the AFE section 42 becomes delayed, the respective correction values become smaller.

Processing performed by the CPU 44 in the present embodiment is similar to the processing illustrated in FIGS. 5 and 7 in the first embodiment. In processing for inputting temperature information from a temperature sensor (S1 and S12) in FIGS. 5 and 7, pieces of temperature information from the two temperature sensors 24 and 46 are inputted, and the CPU 44 reads correction values corresponding to a combination of the temperatures from the EPROM 45 and outputs the correction values to a TG section 55.

Accordingly, the CPU 44, which is a timing adjusting section, adjusts timings of sample-and-hold signals (SH1 and SH2) and a conversion timing signal ADCK provided to the A/D section 53, which are generated by the TG section 55, based on the temperature T1 of the distal end portion 11a and the temperature T2 of the body portion 12.

In the present embodiment, also, timings of the respective timing signals (SH1, SH2 and ADCK) may be adjusted using correction values for correcting pulse widths of the respective timing signals (SH1, SH2 and ADCK) instead of phases of the respective timing signals (SH1, SH2 and ADCK).

Furthermore, in the present embodiment, also, the timings of the respective timing signals (SH1, SH2 and ADCK) may be adjusted using correction values for correcting the pulse widths of the respective timing signals (SH1, SH2 and ADCK) together with the timings (that is, phases) of the respective timing signals (SH1, SH2 and ADCK).

Furthermore, although the above-described example is an example in which the timing pulse signals SH1, SH2 and ADCK are corrected, as in the first embodiment, timings (that is, phases) of drive pulse signals (RG, H1 and H2) may be corrected.

Figure 11:
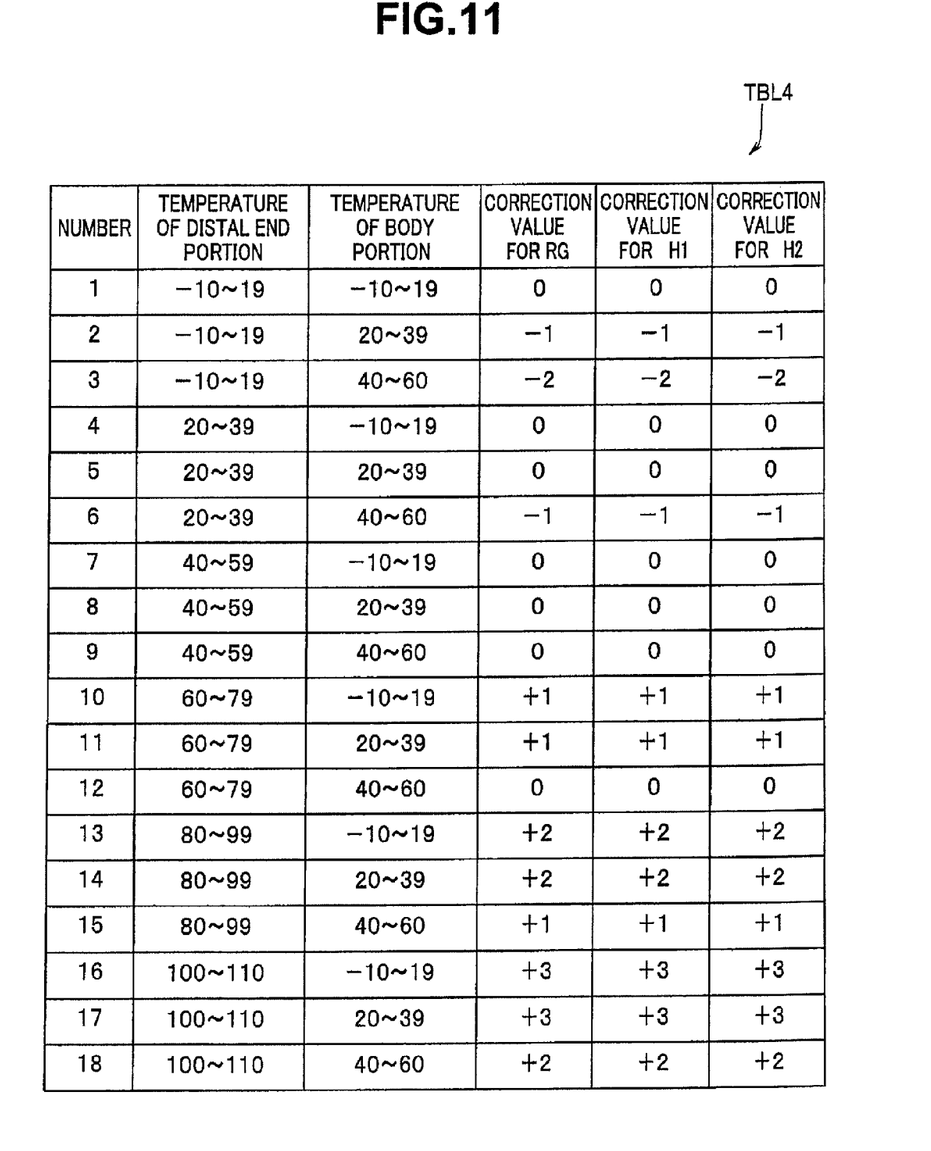
FIG. 11 is a diagram illustrating an example of a table of correction values for timings of drive pulse signals (RG, H1 and H2), which is stored in the EPROM 45, according to the second embodiment of the present invention.

FIG. 11 is a diagram illustrating an example of a table of correction values for timings of drive pulse signals (RG, H1 and H2), which is stored in the EPROM 45. A correction value table TBL4 stores respective correction values for drive pulse signals (RG, H1 and H2) supplied to a CCD 22.

Where the correction value table in FIG. 11 is used, also, the endoscope apparatus 1A can perform proper correlated double sampling processing by means of processing similar to the processing described in the first embodiment.

Furthermore, in the present embodiment, also, the timings (that is, phases) of the drive pulse signals (RG, H1 and H2) may be adjusted together with the timings (that is, phases) or the pulse widths (or both of the phases and the pulse widths) of the sample-and-hold signals (SH1 and SH2). In other words, timings of both the sample-and-hold signals (SH1 and SH2) and the drive pulse signals (RG, H1 and H2) may be adjusted so that correlated double sampling processing is properly performed.

Therefore, according to the present embodiment, an endoscope apparatus enabling correlated double sampling processing to be properly performed in the CDS section 51 even if the distal end portion 11a and the body portion 12 are distant from each other and are used under different temperature environments can be provided.

Furthermore, the contents of variation 1 and variation 2 described in the first embodiment can be applied also to the present embodiment.

According to the above-described embodiments and variations, an electronic endoscope apparatus includes an elongated insertion portion, the electronic endoscope apparatus enabling correlated double sampling processing to be properly performed even if a distal end portion of an insertion portion of an endoscope is used in various temperature ranges can be provided.

The present invention is not limited to the above-described embodiments, and various variations and alterations, etc., are possible without departing from the spirit of the present invention.

What is claimed is:

1. An electronic endoscope apparatus comprising:
   an image pickup device provided in a distal end portion of an insertion portion of an endoscope;
   a first temperature detection section that detects a first temperature of the distal end portion;
   a correlated double sampling section provided in a body portion to which a proximal end of the insertion portion of the endoscope is connected, the correlated double sampling section extracting a signal component from an image signal outputted from the image pickup device;
   a cable that transmits an electric signal between the distal end portion and the body portion;
   a timing generating section provided in the body portion, the timing generating section generating a sample-and-hold signal for operating the correlated double sampling section and a drive pulse signal for driving the image pickup device; and
   a timing adjusting section that determines whether or not a predetermined time period has elapsed, and upon determining that the predetermined time period has elapsed, adjusts a timing of the sample-and-hold signal generated by the timing generating section, based on the first temperature detected by the first temperature detection section.

2. The electronic endoscope apparatus according to claim 1, further comprising a second temperature detection section that detects a second temperature of the body portion, wherein the timing adjusting section adjusts the timing of the sample-and-hold signal based on the first and second temperatures.

3. The electronic endoscope apparatus according to claim 1, wherein the timing adjusting section adjusts the timing of the sample-and-hold signal by changing a phase or a pulse width of the sample-and-hold signal.

4. The electronic endoscope apparatus according to claim 1, wherein the timing adjusting section further adjusts a timing of the drive pulse signal based on the first temperature, by changing a phase of the drive pulse signal.

5. The electronic endoscope apparatus according to claim 1, wherein the timing adjusting section adjusts the timing of the sample-and-hold signal by changing a phase or a pulse width of the sample-and-hold signal.

6. The electronic endoscope apparatus according to claim 1, further comprising an analog-digital conversion section that converts the image signal, which is an analog signal outputted from the correlated double sampling section, to a digital signal,
wherein the timing adjusting section further adjusts a timing of a conversion timing signal inputted to the analog-digital conversion section.

7. The electronic endoscope apparatus according to claim 1, wherein the timing adjusting section refers to a table storing a correction value for correcting the timing of the sample-and-hold signal, and adjusts the timing of the sample-and-hold signal using a correction value according to the first temperature, the correction value being read from the table.

8. The electronic endoscope apparatus according to claim 2, wherein the timing adjusting section refers to a table storing a correction value for correcting the timing of the sample-and-hold signal, and adjusts the timing of the sample-and-hold signal using a correction value according to a combination of the first temperature and the second temperature, the correction value being read from the table.

9. The electronic endoscope apparatus according to claim 1, further comprising a temperature display section that displays the first temperature.

10. The electronic endoscope apparatus according to claim 1, further comprising a waveform shaping circuit provided in the distal end portion, the waveform shaping circuit shaping a waveform of the drive pulse signal supplied to the image pickup device.

11. The electronic endoscope apparatus according to claim 1, wherein the adjustment of the timing of the sample-and-hold signal is made during a video blanking period.

12. The electronic endoscope apparatus according to claim 2, wherein the timing adjusting section adjusts the timing of the sample-and-hold signal by changing a phase or a pulse width of the sample-and-hold signal.

13. The electronic endoscope apparatus according to claim 2, wherein the timing adjusting section further adjusts a timing of the drive pulse signal based on the first temperature, by changing a phase of the drive pulse signal.

14. The electronic endoscope apparatus according to claim 2, wherein the timing adjusting section adjusts the timing of the sample-and-hold signal by changing a phase or a pulse width of the sample-and-hold signal.

15. The electronic endoscope apparatus according to claim 2, further comprising an analog-digital conversion section that converts the image signal, which is an analog signal outputted from the correlated double sampling section, to a digital signal,
wherein the timing adjusting section further adjusts a timing of a conversion timing signal inputted to the analog-digital conversion section.

16. The electronic endoscope apparatus according to claim 2, further comprising a temperature display section that displays at least one of the first temperature and the second temperature.

17. The electronic endoscope apparatus according to claim 2, further comprising a waveform shaping circuit provided in the distal end portion, the waveform shaping circuit shaping a waveform of the drive pulse signal supplied to the image pickup device.

18. The electronic endoscope apparatus according to claim 2, wherein the adjustment of the timing of the sample-and-hold signal is made during a video blanking period.

\* \* \* \* \*